United States Patent [19]

Kaneshima et al.

[11] Patent Number: 5,476,997
[45] Date of Patent: Dec. 19, 1995

[54] EXTENDED HUMAN HEMATOPOIESIS IN A HETEROLOGOUS HOST

[75] Inventors: Hideto Kaneshima; Reiko Namikawa, both of Palo Alto; Joseph M. McCune, San Francisco, all of Calif.

[73] Assignee: Systemix, Inc., Palo Alto, Calif.

[21] Appl. No.: 245,250

[22] Filed: May 17, 1994

Related U.S. Application Data

[63] Continuation of Ser. No. 836,195, Feb. 13, 1992, abandoned, which is a continuation of Ser. No. 347,912, May 5, 1989, abandoned.

[51] Int. Cl.$^6$ .................................................. A61K 35/00
[52] U.S. Cl. ........................ 800/2; 424/553; 424/580; 424/582; 424/577; 424/520; 424/578; 800/DIG. 2; 800/DIG. 5
[58] Field of Search .............................. 424/9, 553, 577, 424/580, 582; 800/2, DIG. 2, DIG. 5

[56] References Cited

PUBLICATIONS

Pollard; Tokai J. Exp. Clin. Med. 10(2,3):175–179 (1985).
Wade et al., Transplantation 44(1):88–92 (1987).
Fohlmeister et al., Nat. Immun. Cell Growth Regul. 4:221–228 (1985).
McCune et al., Science 241:1632–1639 (1988).
Povlsen et al., Nature 248:247–249 (1974).
Bosma et al., Nature 301:527–530 (1983).
Mosier et al., Nature 335:256–259 (1988).

Primary Examiner—Jasemine C. Chambers
Attorney, Agent, or Firm—Bertram I. Rowland; Pamela J. Sherwood

[57] ABSTRACT

A human hematopoietic system is provided in an immunocompromised mammalian host, where the hematopoietic system is functional for extended periods of time. Particularly, human fetal liver tissue and human fetal thymus is introduced into an appropriate site of a young immunocompromised mouse at a site supplied with a vascular system, whereby the fetal tissue results in novel formation of functional human bone marrow tissue.

6 Claims, No Drawings

EXTENDED HUMAN HEMATOPOIESIS IN A HETEROLOGOUS HOST

This is a continuation of application Ser. No. 07/836,195 filed Feb. 13, 1992 now abandoned which is a continuation of application Ser. No. 07/347,912 filed May 5, 1989 now abandoned.

TECHNICAL FIELD

The technical field of the subject invention is the production of human hematopoietic poietic cells.

BACKGROUND

Until very recently, the source of a wide variety of natural products was the native host. For the most part, proteins, particularly factors, were isolated from blood obtained from donors. The blood could be used for transfusions, providing a source of red blood cells. In addition, numerous blood factors which were extracted were used in the treatment of a host of diseases, such as hemophilia, thallasemia, other globin diseases, and the like. In many instances, particularly during surgery, the infusion of platelets is desirable. In cases of cancer of the bone marrow, there is substantial interest in being able to replace the neoplastic bone marrow with normal bone marrow.

Because of the central role that the hematopoietic system plays, there are frequent needs for the use of one or more of the hematopoietic lineages in the treatment of a patient. Furthermore, immature hematopoietic cells may serve in the investigation of the amplification, differentiation, and maturation of hematopoietic cells. Allogeneic stem cells may serve in the production of mature cells in a host deficient in one or more lineages or in stem cells. There is, therefore, substantial interest in being able to produce hematopoietic cells.

RELEVANT LITERATURE

References concerned with immunoincompetent hosts, particularly CID, or SCID hosts include McGuire et al., *Clin. Immunol. and Immunopath.* (1975) 3:555–566; Perryman and Torbeck, *J. Am. Vet. Med. Assoc.* (1980) 176:1250–1251; Schultz and Sidman, Genetically-determined Murine Models of Immunodeficiency, The Jackson Laboratory, Bar Harbor, Me.; Bosma et al., *Nature* (1983) 301:527–530; Custer et al., *Amer. J. Path.* (1985) 120:464–477; Dorshkind et al., *J. of Immunol.* (1985) 134:3798–3801; Kerghtley et al., *Lancet*, Nov. 1, 1975, 850–853; Touraine, *Immunological Rev.* (1983) 71:103–121; and Fulop and Phillyes, *J. of Immunology* (1986) 136:4438–4443.

References concerned with xenogeneic cells growing within live hosts include Krueger et al., *J. Inv. Dermatol.* (1975) 64:307–312; Krueger et al., *Proc. Natl. Acad. Sci U.S.A.* (1983) 80:1650–1654; Krueger and Shelby, *J. Inv. Dermatol.* (1981) 76:506–510; Ware et al. *J. Immunol. Meth.* (1985) 85:353–361; Ford et al., *Nature* (1956) 177:452–454; Dovlsen et al., *Nature* (1974) 248:247–249; Mannhardt et al., *Thymus* (1982) 4:209–220; Schulte-Wisserman et al., *Scand. J. Immunol.* (1978) 8:387–396. Please specifically note, McCune et al., *Science* (1988) 241:1632–1639 and the comment therein; Yancopoulos and Alt, *Ibid* (1988) 241:1581–1583, and references cited therein.

See also copending application Ser. No. 287,075, filed Dec. 20, 1987, and EPO 88.312222.8, which are incorporated herein by reference.

SUMMARY OF THE INVENTION

Methods and compositions are provided for the production of human bone marrow equivalent in a heterologous host. The method comprises combining fetal tissue from liver and thymus in an immunocompromised mammalian host, whereby the liver tissue grows and matures to provide hematopoietic cells in conjunction with stromal cells. The resulting bone marrow equivalent gives rise to cells which populate the heterologous immunocompromised host for extended periods of time with human hematopoietic lineages.

DESCRIPTION OF THE SPECIFIC EMBODIMENTS

Methods and compositions are provided for the production of human hematopoietic cells with a plurality of lineages in a immunocompromised heterologous mammalian host, particularly a mouse, for extended periods of time. The method comprises combining non-dispersed fetal liver tissue and thymus tissue in juxtaposition in an appropriate site in the immunocompromised host. The liver tissue is found to amplify, differentiate, and mature within discrete anatomic locations of the growing human fetal thymus, as evidenced by collections of cells of various hematopoietic lineages and stromal cells. The type, quantity, and spatial organization of these hematopoietic and stromal cells is similar to that found in normal human bone marrow. Thus, these "bone marrow equivalents" are found to include immature blast cells (likely to be inclusive of early hematolymphoid precursors), cells of the myelomonocytic lineage including polymorphonuclear granulocytes and eosinophilic granulocytes, cells of the megakaryocytic lineage, cells likely to be within the lymphoid lineage, immature adipocytes and undefined stromal cells. These bone marrow equivalents remain functional for periods of at least about 12 months, usually at least about 13 months or more. Thus, the nature of the bone marrow equivalents supports the presence of the human pluripotent hematopoietic stem cell.

Of particular interest as the heterologous host is an immunocompromised mouse host. A wide variety of immunocompromised mice host exists, including SCID, nude mice, irradiated mice, and the like. Of particular interest are the SCID mice. Other immunocompromised animals include CID (combined immunodeficiency) horses, CID hosts, where the host may be immunocompromised because of a naturally occurring genetic defect, irradiation, chemical treatment, transgeneic manipulation, or the like.

As exemplary of immunocompromised host is the mouse. In referring to a mouse host it should be understood that other immunocompromised animals may be employed where the animal is incapable of producing competent B- and/or T-cells. This may be as a result of lack of Class I and/or II major histocompatibility complex antigens, lack of stem cells, lack of recombinase, or any other lesion. The mouse host is grafted with both fetal liver and thymus tissue, where the tissue implants are normally contiguous. While any vascularized convenient site for implantation may be employed, of particular interest is the renal capsule, which provides a sanctuary for the tissue. Methods of inserting tissue into the renal capsule have been described in the literature and are substantially described in application Ser.

No. 287,075 indicated above. The tissue will generally be slices of a size in the range of about 0.5 to 4 mm, more usually 1 to 2 mm, with a thickness in the range of about 1 to 2 mm for implantation with a 15- to 20-gauge trocar. Generally, the fetal tissue will be of an age in the range of at least about 7 gestational weeks generally about 9 to 24 g.w. For liver tissue, the age will generally be from about 10 to 24 g.w., more usually 13 to 22 g.w., while for thymus tissue, the age will generally be in the range of about 9 to 24 g.w., more usually less than 20 g.w.

Other tissues or cells may be introduced into the host, particularly lymph node tissue. The lymph node tissue may also be included in the renal capsule, but may also be placed at other sites, such as the pancreas or the 4th mammary fat pad. The fetal lymph node tissue will generally be of an age in the range of about 16 to 20 g.w. Of particular interest is to introduce fetal bone, which will usually be of an age in the range of about 15 g.w. to 24 g.w. The fetal bone will be of a size of about 2 to 5 mm in diameter and 1 to 20 mm in length. The bone will usually be placed subcutaneously and may be located at any convenient place in the mouse, particularly subcutaneously.

The bone may serve as a repository of the hematopoietic and stromal cells, so that the bone marrow which is formed in the renal capsule may migrate to the bone and populate the bone, much as occurs in the normal human fetus. In this way, bone can be produced, which is of human origin and is populated with human hematopoietic and stromal cells.

The tissue may be fresh or frozen tissue (−70° C.), normally frozen within 12 hrs. of collection. The frozen tissue may be stabilized with suitable preservation agents, and DMSO may be added. Alternatively, the tissue may come from tissue implanted in an immunocompromised host. The introduction of the tissue will occur with a host at an age less than about 25% of its normal lifespan, usually to 20% of the normal lifespan with mice, the age will generally be of an age of about 3 to 10 weeks, more usually from about 4 to 8 weeks. The mice may be either sex, may be neutered, and may be otherwise normal, except for the immunocompromised state, or may have one or more mutations, which may be naturally occurring or a result of mutagenesis.

The mice containing the transplanted bone marrow equivalent may be used in a wide variety of ways. Mice may be used to study the effect of drugs on immune status or a particular type of hematopoietic cells, particularly the development of hematopoietic lineages. In addition, the mouse may be used to titrate activity of various compositions, such as particular growth factors, stimulating factors, or the like where such factors are found to have an effect on differentiation and/or multiplication of particular cells. The cells may also be harvested and used for transfusion in a particular host, either directly or after amplification and/or selection. The human hematopoietic system may also be used to develop vaccines to determine particular oligopeptides which are effective with particular MHC antigen restricted T-cells. In addition, the B-cells which are produced may be used for immunization, so as to provide a source of immunoglobulin directed to a specific antigen. Also, the populations found in the mouse, e.g., bone marrow, may be used to give rise to all elements of the human (fetal and adult) hematopoietic system, including the lineages of lymphocytes, erythrocytes, myelomonocytes, megakaryocytes and platelets. In addition, the bone marrow may be used as a source of stromal cells, from which cells may be used for in vitro culturing of the hematopoietic cells. Further, these stromal cells may be used as a source of growth factors, which are related to the self-renewal or differentiation of progenitor hematopoietic cells.

Because the subject mice are able to maintain the hematopoietic lineages for long periods of time, they may be used to study a wide variety of drugs, diseases, treatments of such diseases, the etiology of diseases, and the like. In this manner, insight may be obtained as to the causes of various disease responses as well as methods for counteracting the disease causing elements.

The following examples are offered by way of illustration and not by way of limitation.

EXPERIMENTAL

Whole human fetal liver fragments of a size of about 4 mm ×6 mm containing all of the representative cells of this organ (microenvironmental stromal cells, hematopoietic stem cells and their progeny, as well as hepatocytes) were surgically implanted into the renal capsule of SCID mice (C.B17 scid/scid mice) along with whole human fetal thymus fragments of a size of about 2 mm ×2 mm. The fragments were from a fetus of under about 24 gestational weeks.

The tissue was obtained directly in the operating room as fetal parts. Without maintaining strict sterility the parts were taken immediately to a gross dissection room. The identified tissue was dissected out and placed into RPMI 1640 medium with 10% fetal cell serum. The organs were then cut into approximately 1×4 mm for insertion using a 19 gauge trocar. The mice are anesthetized with halothane, a 1 cm incision made to expose the kidney and the tissue introduced by means of the trocar beneath the kidney capsule. The fragments were placed in close proximity so as to be in contact. The mouse was allowed to grow over a period of 13 months, while maintained on a normal diet using trimethoprim/ sulfamethoxazole (40 mg/200 mg per 5 ml of suspension; 0.125 ml of suspension per 4 ml of drinking water per mouse per day). At the end of 13 months, the mouse was checked and it was found that the peripheral circulation of the mouse contained human T cells. The maintenance of human stem cell self-renewal and differentiation in the SCID-hu mouse requires microenvironmental input from the fetal liver stroma. Histological examination of the implanted fetal thymus showed that the fetal liver stroma had grown into the substance of the thymus, setting up an hematopoietic environment virtually indistinguishable from that found in bone marrow itself. Included within these "bone marrow islands" are found immature blast cells (likely to be inclusive of early hematolymphoid precursors), cells of the myelomonocytic lineage including polymorphonuclear granulocytes and eosinophilic granulocytes, cells of the megakaryocytic lineages, cells likely to be within the lymphoid lineage, immature adipocytes, and undefined stromal cells. The continuation of these islands for periods of time lasting over 13 months indicates that human pluripotent hematopoietic stem cells are present as well. In contrast, when the hematopoietic cells of fetal liver are given alone, in the absence of the stromal cells of the organ, bone marrow equivalents are not seen and T cells are only found in the periphery for a period of time ranging from 4 to 13 weeks.

It is evident from the above results, that novel mice are provided which comprise cellular structures which appear as human bone marrow as a tissue slice under a microscope and comprises the same type of cells associated with bone marrow, so as to be a source of all of the human hematopoietic lineages, as well as stem cells and stromal cells. The bone marrow is stable for long periods of time, so as to be a continuous supply of such cells and allows for various studies of the various lineages and the effect of drugs and factors on the viability, amplification, and differentiation of such cells.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of producing human bone marrow equivalent comprising:

introducing into a vascularized site of a C.B-17 scid/scid mouse host human fetal liver and human fetal thymus tissue in juxtaposition; and maintaining said C.B-17 scid/scid mouse host in a viable state, whereby cells of said human fetal liver and human fetal thymus tissue form into bone marrow equivalent.

2. A method according to claim 1, wherein said C.B-17 scid/scid mouse host further comprises a human fetal lymph node.

3. A method for producing mature cells of a multiplicity of human hematopoietic lineages, said method comprising:

introducing into a vascularized site of a C.B-17 scid/scid mouse host human fetal liver and human fetal thymus tissue in juxtaposition; and maintaining said C.B-17 scid/scid mouse host in a viable state, whereby cells of said human fetal liver and human fetal thymus tissue form into bone marrow equivalent, migrate into the peripheral circulation and differentiate and mature to mature cells of a multiplicity of human hematopoietic lineages.

4. A method according to claim 3, wherein one of said human hematopoietic lineages is the lymphoid lineage.

5. A C.B-17 scid/scid mouse host comprising a viable human bone marrow equivalent capable of providing mature cells of a multiplicity of hematopoietic lineages, wherein said human bone marrow equivalent is comprised of human fetal thymus and human fetal liver tissue grown in juxtaposition, wherein said bone marrow equivalent is prepared by the contiguous co-implantation of said human fetal thymus and human fetal liver tissue.

6. A C.B-17 scid/scid mouse host according to claim 5, further comprising mature cells of a multiplicity of human hematopoietic lineages derived from said bone marrow equivalent.

* * * * *